Figure 1:
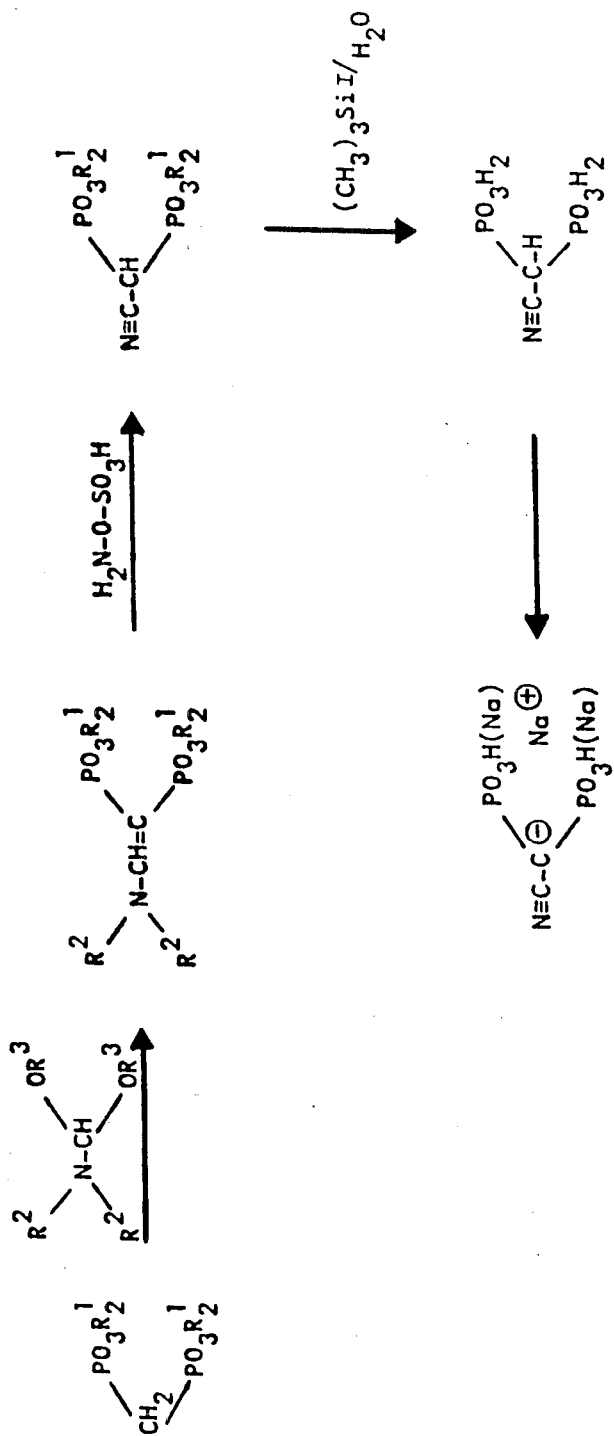
Figure 2:
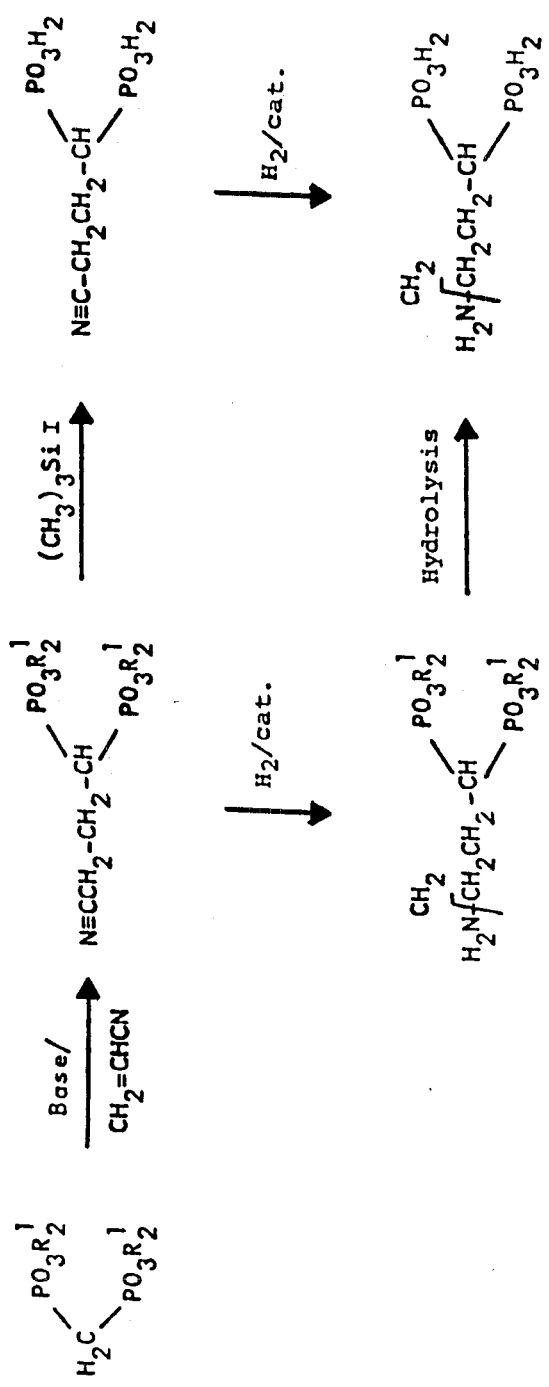

United States Patent [19]

Biere et al.

[11] Patent Number: 4,645,762

[45] Date of Patent: Feb. 24, 1987

[54] DIPHOSPHONIC ACID DERIVATIVES AND PHARMACEUTICAL PREPARATIONS CONTAINING SAME

[75] Inventors: Helmut Biere; Clemens Rufer, both of Berlin; Irmgard Boettcher, Basel, all of Fed. Rep. of Germany

[73] Assignee: Schering Aktiengesellschaft, Berlin and Bergkamen, Fed. Rep. of Germany

[21] Appl. No.: 511,116

[22] Filed: Jul. 5, 1983

[30] Foreign Application Priority Data

Jul. 5, 1982 [DE] Fed. Rep. of Germany ....... 3225469

[51] Int. Cl.$^4$ .......................... A61K 31/66; C07F 9/40
[52] U.S. Cl. ..................................... 514/108; 558/158
[58] Field of Search ......................... 260/932; 424/204; 514/108; 558/158

[56] References Cited

U.S. PATENT DOCUMENTS 3,813,456  5/1974  Kerst ................................... 260/968

Primary Examiner—Anton H. Sutto
Attorney, Agent, or Firm—Millen & White

[57] ABSTRACT

Diphosphonic acid derivatives of the formula

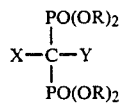

wherein
X is cyano, 2-cyanoethyl, or 3-aminopropyl and Y is H, or X and Y together represent dimethylaminomethylene ($(CH_3)_2NCH=$), and
R is hydrogen, alkyl of 1-4 carbon atoms, or a cation derived from a base, especially an alkali metal atom,
excluding the cyanomethanebis (phosphonic acid diethyl ester),
are pharmacologically active compounds.

23 Claims, 2 Drawing Figures

DIPHOSPHONIC ACID DERIVATIVES AND PHARMACEUTICAL PREPARATIONS CONTAINING SAME

The present invention relates to diphosphonic acid derivatives, a process for their production, and to pharmaceutical preparations containing them.

SUMMARY OF THE INVENTION

It is an object of this invention to provide such compounds having valuable pharmacological properties.

Upon further study of the specification and appended claims, further objects and advantages of this invention will become apparent to those skilled in the art.

These objects have been achieved by providing diphosphonic acid derivatives of the formula

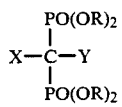

wherein
X is cyano, 2-cyanoethyl, or 3-aminopropyl and Y is H, or X and Y together represent dimethylaminomethylene (($CH_3)_2NCH=$), and
R is hydrogen, alkyl of 1–4 carbon atoms, or a cation derived from a base, especially an alkali metal atom,
excluding the cyanomethanebis(phosphonic acid diethyl ester).

DETAILED DISCUSSION

The compounds of this invention surprisingly exhibit a pronounced antiinflammatory and antiarthritic activity in mammals, including humans. Moreover, they are distinguished in that they are capable, inter alia, of affecting the constructive and destructive power of the bone cells (osteoblasts/osteoclasts) in such a way that curative effects can clearly be proven to be caused by them in rats with induced arthritis.

This antiarthritic activity of the compounds of this invention forms a basis for therapy of rheumatoid arthritis, osteoarthritis, spondylitis ankylosans, and other related diseases, especially of the collagen and skeletal system (e.g., osteoporosis, Paget's disease, etc.). Moreover, the phosphonates, being good complex-forming compounds for calcium, can be employed with therapeutic efficacy in all cases where a disturbed Ca metabolism has been recognized as the cause for a disease, for example in cardiovascular diseases, ectopic calcifications, etc.

The dosage of the compounds of this invention is 1–50 mg/kg/day when administered to humans for their antiarthritic effects; and is 1–50 mg/kg/day when administered to humans for their antiinflammatory effects; and 1–50 mg/kg/day when administered for their calcium-metabolism related effects. Administration of the compounds, e.g., for their antiarthritic and antiinflammatory activity, is analogous to that of the known agents indomethacin and naproxen.

The compounds of this invention can be utilized in the form of their esters (e.g., methyl, ethyl, propyl, isopropyl, butyl, secbutyl, isobutyl, etc.), e.g., mono-, di-, tri- or tetraesters, usually tetraesters, i.e., bis(phosphonic acid dialkyl esters), but preferably in the form of the free phosphonic acids and/or their physiologically compatible salts with alkali metal hydroxides (e.g., of Na, K), alkaline earth metal hydroxides (e.g., Ca), or the usual compatible organic bases. These include their mono-, di-, tri-, tetra and penta-salts. The various esters and salts can be conventionally prepared as discussed below with conventional control of the relative proportion of reactants. Usually, mixtures are obtained which can be used pharmacologically. However, it is preferred that the desired salt or ester be conventionally separated using conventional separation techniques.

Suitable galenic formulations include capsules, tablets, dragees, suppositories, and also injection solutions and dermal preparations. Also local application for the treatment of dermal or systemic diseases is possible.

The medical specialties are prepared in the usual way by converting the active agents into the desired forms of application with suitable additives, e.g., solutions, lotions, ointments, creams, or plasters. In the thus-formulated medicines, the concentration of active compound is dependent on the type of application. In the case of lotions and ointments, an active agent concentration of 0.001% to 1% is preferably employed. Administration is as conventional with such topical formulations.

The novel compounds are also suitable furthermore in the form of capsules, tablets, or dragees, containing preferably 10–200 mg of active agent and being administrable orally.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The preparation of the diphosphonic acid derivatives of this invention takes place according to methods well-known to those skilled in the art. These include the following:

a process for the preparation of diphosphonic acid derivatives of Formula I $$\begin{array}{c} PO(OR)_2 \\ | \\ X-C-H \\ | \\ PO(OR)_2 \end{array} \quad (I)$$

wherein
X is cyano or dimethylaminomethylene and
R is hydrogen, an alkali metal atom (or other cation of a base), or an alkyl group of 1–4 carbon atoms, except for the cyanomethanebis(phosphonic acid diethyl ester),
comprising conventionally reacting a dimethylformamide dialkyl acetal of Formula II $$(CH_3)_2NCH(OR')_2 \quad (II),$$

wherein R' is an alkyl group of 1–4 carbon atoms, with a methanebis(phosphonic acid dialkyl ester) of Formula III $$CH_2(PO_3R_2)_2 \quad (III),$$

wherein R is as defined above, and, optionally, treating the resultant enamine with hydroxylamine-O-sulfonic acid, saponifying any ester groups present, and/or converting the free acids into the salts thereof;
or
a process for the preparation of diphosphonic acid derivatives of Formula I $$\begin{array}{c} PO(OR)_2 \\ | \\ X-C-H \\ | \\ PO(OR)_2 \end{array} \quad (I)$$

wherein
X is 2-cyanoethyl or 3-aminopropyl and
R is hydrogen, an alkali metal atom (or other cation of a base), or an alkyl group of 1–4 carbon atoms,
comprising conventionally reacting a methanebis(phosphonic acid dialkyl ester) of Formula IV $$CH_2(PO_3R_2)_2 \quad (IV),$$

wherein R is as defined above, with acrylonitrile and, optionally, in any desired sequence, reducing the resultant nitriles to the corresponding amines and/or saponifying the resultant esters and/or converting the free acids into the salts thereof.

In the charts, $R^2$ is $CH_3$, $R^3$ is $C_{1-4}$-alkyl and R' is R as defined above.

The reaction of the dimethylformamide dialkyl acetals of Formula II with the methanebis(phosphonic acid dialkyl esters) of Formula III to obtain the corresponding enamines can be conducted in a manner known per se (see, for example, Enamines, G. Cook, Marcel-Dekker Publishers, New York and London, 1969; Chem. Ber. 101: 1968), for example by heating the components in the presence of bases (potassium tert-butylate, etc.).

The optionally following reaction of the enamines is likewise effected under conditions well-known to persons skilled in the art (see, e.g., European Patent Application No. 16 978), for example by reacting these compounds in an aqueous solution at a pH of 0 to 1 with the hydroxylamine-O-sulfonic acid.

The optionally subsequently conducted saponification of the esters can be accomplished by means of mineral acids (e.g. semiconcentrated hydrochloric acid or sulfuric acid). The cleavage takes place in an especially gentle way in an inert solvent (e.g., diethyl ether, diisopropyl ether, dioxane, tetrahydrofuran, dichloromethane, chloroform, or carbon tetrachloride) with trimethylsilyl iodide. For salt formation, the free acids are reacted in the usual way with the corresponding bases.

The condensation of the methanebis(phosphonic acid dialkyl esters) of Formula IV with acrylonitrile takes place under the conditions usually employed for cyanoethylation of active methylene compounds. Thus, it is possible, for example, to convert compounds of Formula IV in an inert solvent (diethyl ether, diisopropyl ether, dioxane, tetrahydrofuran, etc.) with sodium, potassium, or the hydrides thereof, into their salts, and to react these with acrylonitrile.

The optionally following reduction of the nitriles to the corresponding amines likewise takes place under conditions well-known to those skilled in the art. Thus, the nitriles can be hydrogenated, for example, with hydrogen in the presence of nickel or platinum catalysts, or they can be reduced with complex metal hydrides, such as, for example, lithium aluminum hydride.

All of the starting materials used in the preparations of this invention are known and/or conventionally preparable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2-Dimethylaminoethene-1,1-bis(phosphonic Acid Diethyl Ester)

A mixture of 2.9 g (20 millimoles) of dimethylformamide diethylacetal and 2.9 g (10 mmol) of methanebis(phosphonic acid diethyl ester) is combined with 110 mg of potassium tert-butylate and heated under nitrogen for one hour to 120° C. (bath temperature). Thereafter the thus-obtained ethanol as well as the excess acetal are distilled off under vacuum. A light-colored oil remains; yield 3.4 g.

EXAMPLE 2

Cyanomethanebis(phosphonic Acid Diethyl Ester)

A solution of 45.2 g (0.4 mole) of hydroxylamine-O-sulfonic acid in 400 ml of water is combined with 68.6 g (0.2 mol) of 2-dimethylaminoethene-1,1-bis(phosphonic acid diethyl ester) and stirred for 30 minutes at room temperature, whereafter it is quickly extracted with 3×100 ml of dichloromethane. (The organic extracts are discarded.) The aqueous phase is combined with 100 ml of dichloromethane and further stirred overnight at room temperature. After separating the organic phase and concentration, 37 g is obtained.

The aqueous phase is again stirred with 100 ml of dichloromethane overnight, worked up as set forth above, and yields 19 g.

A third treatment of the same kind leads to 9 g of product. Thus, 65 g is produced in total.

After bulb tube distillation at 170°–175° C. and under 0.01 mm of pressure, 49.4 g is obtained.

EXAMPLE 3

Cyanomethanediphosphonic Acid, Trisodium Salt

A solution of 6.3 g (20 mmol) of cyanomethanebis(phosphonic acid diethyl ester) in 30 ml of carbon tetrachloride is combined under a nitrogen atmosphere at 0° C. dropwise with 12 ml of iodotrimethylsilane and thereafter agitated for one hour at room temperature. After concentration, the residue is combined with acetone and water and again concentrated under vacuum. By extraction with dichloromethane, iodine-containing impurities are separated; then the water-soluble material is combined with 5 g of sodium bicarbonate, and finally the thus-produced trisodium salt is precipitated from the aqueous solution by the addition of ethanol. Yield 3.74 g, mp above 300° C.

The free cyanomethane-1,1-diphosphonic acid can be obtained as an oil by treating the sodium salt with the ion exchanger "Amberlite" IR 120.

EXAMPLE 4

3-Cyanopropane-1,1-bis(phosphonic Acid Diethyl Ester)

A suspension of 2.4 g of sodium hydride (80%) in 100 ml of dimethoxyethane is combined at 0° C. dropwise with a solution of 23.1 g of methanebis(phosphonic acid diethyl ester) in 20 ml of dimethoxyethane. After gas evolution has ceased, the mixture is stirred for another 15 minutes at 0°0 C., then combined with 4.25 g of acrylonitrile, and heated for 5 hours to 80° C. After allowing the mixture to stand overnight, it is combined with 5 ml of glacial acetic acid, then the dimethoxyethane is distilled under vacuum, and the residue is chromatographed on silica gel (toluene-acetone). The nitrile fraction is subsequently distilled once more on a bulb tube (boiling point 180°–190° C., 0.03 mm). Yield 12 g.

EXAMPLE 5

3-Cyanopropane-1,1-bis(phosphonic Acid), Disodium Salt

Analogously to Example 3, 3-cyanopropane-1,1-bis(phosphonic acid diethyl ester) [Example 4] yields 3-cyanopropane-1,1-diphosphonic acid by cleavage with iodotrimethylsilane, and this product is converted into the disodium salt. Yield 71%, mp above 300° C.

EXAMPLE 6

4-Aminobutane-1,1-bis(phosphonic Acid Diethyl Ester)

A solution of 2.44 g (7.1 mmol) of 3-cyanopropane-1,1-bis(phosphonic acid diethyl ester) in 40 ml of ethanolic hydrochloric acid (0.7N) is combined with 285 mg of platinum dioxide and hydrogenated at room temperature. After absorption of the theoretical quantity of hydrogen, the mixture is vacuum-filtered from the catalyst, the latter is washed with ethanol, and the combined ethanol phase is concentrated under vacuum. The residue is treated with a small amount of water and sodium bicarbonate and extracted exhaustively with dichloromethane. The residue of the dichloromethane phase is 1.9 g.

EXAMPLE 7

4-Aminobutane-1,1-diphosphonic Acid, Disodium Salt

This compound is prepared from the sodium salt of Example 5 by catalytic hydrogenation with platinum dioxide in an aqueous solution. Yield 80%; mp above 300° C. (from dimethylformamide).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating inflammation in a patient in need of such treatment comprising administering to the patient an anti-inflammatorily effective amount of a diphosphonic acid compound of the formula

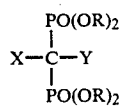

wherein
X is cyano, 2-cyanoethyl, or 3-amino-propyl and Y is H, or X and Y together represent $(CH_3)_2NCH=$ and each R is independently hydrogen or alkyl of 1–4 carbon atoms,
with the proviso that all four R's are not ethyl when X is cyano,
or a pharmaceutically acceptable salt thereof with a base.

2. A method of treating arthritis in a patient in need of such treatment comprising administering to the patient an anti-arthritically effective amount of a diphosphonic acid compound of the formula

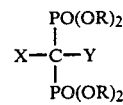

wherein
X is cyano, 2-cyanoethyl, or 3-amino-propyl and Y is H, or X and Y together represent $(CH_3)_2NCH=$ and each R is independently hydrogen or alkyl of 1–4 carbon atoms,
with the proviso that all four R's are not ethyl when X is cyano,
or a pharmaceutically acceptable salt thereof with a base.

3. A method of claim 2, wherein X is cyano or 2-cyanoethyl or X and Y are $(CH_3)_2NCH=$.

4. A method of claim 2, wherein X and Y are $(CH_3)_2NCH=$.

5. A pharmaceutical composition comprising an anti-arthritically effective amount of a diphosphonic acid compound of the formula

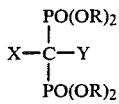

wherein
X is cyano, 2-cyanoethyl, or 3-amino-propyl and Y is H, or X and Y together represent $(CH_3)_2NCH=$ and each R is independently hydrogen or alkyl of 1–4 carbon atoms,
with the proviso that all four R's are not ethyl when X is cyano,
or a pharmaceutically acceptable salt thereof with a base.

6. A composition of claim 5, wherein X is $(CH_3)_2NCH=$, cyano or 2-cyanoethyl.

7. A composition of claim 5, wherein X is cyano or 2-cyanoethyl.

8. A composition of claim 5 adapted for topical administration.

9. A diphosphonic acid compound of the formula

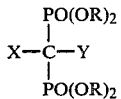

wherein
X is cyano, 2-cyanoethyl, or 3-aminopropyl and Y is H, or X and Y together represent $(CH_3)_2NCH=$,
each R is independently hydrogen or alkyl of 1–4 carbon atoms,
with the proviso that all four R's are not ethyl when X is cyano,
or a pharmaceutically acceptable salt thereof with a base.

10. A compound of claim 9 which is a salt with an alkali metal atom.

11. A compound of claim 9 wherein X is cyano.

12. A compound of claim 9 wherein X is 2-cyanoethyl.

13. A compound of claim 9 wherein X and Y represent dimethylaminomethylene.

14. A compound of claim 9 wherein X is 3-aminopropyl.

15. 2-Dimethylaminoethene-1,1-bis(phosphonic acid diethyl ester), a compound of claim 9.

16. Cyanomethanediphosphonic acid, a compound of claim 9.

17. Trisodium salt of cyanomethanediphosphonic acid, a compound of claim 9.

18. 3-Cyanopropane-1,1-bis(phosphonic acid diethyl ester), a compound of claim 9.

19. 3-Cyanopropane-1,1-bis(phosphonic acid), a compound of claim 9.

20. Disodium salt of 3-cyanopropane-1,1-bis(phosphonic acid), a compound of claim 9.

21. 4-Aminobutane-1,1-bis(phosphonic acid diethyl ester), a compound of claim 9.

22. 4-Aminobutane-1,1-bis-diphosphonic acid, a compound of claim 9.

23. Disodium salt of 4-aminobutane-1,1-bis-diphosphonic acid, a compound of claim 9.

* * * * *